United States Patent
Kontur et al.

(10) Patent No.: US 11,931,244 B2
(45) Date of Patent: Mar. 19, 2024

(54) DIFFRACTIVE ARTIFICIAL OPHTHALMIC LENS WITH OPTIMISED APODIZATION AND METHOD FOR THE PRODUCTION OF SUCH ARTIFICIAL OPHTHALMIC LENS

(71) Applicant: MEDICONTUR ORVOSTECHNIKAI KFT., Zsambek (HU)

(72) Inventors: Laszlo Ferenc Kontur, Budapest (HU); Bence Papdi, Szeged (HU); Peter Koncsar, Budapest (HU); Daniel Bercsenyi, Erd (HU); Balazs Fekete, Gyal (HU); Gabor Erdei, Budapest (HU)

(73) Assignee: MEDICONTUR ORVOSTECHNIKAI KFT., Zsambek (HU)

( * ) Notice: Subject to any disclaimer, the term of this patent is extended or adjusted under 35 U.S.C. 154(b) by 631 days.

(21) Appl. No.: 16/958,306

(22) PCT Filed: Dec. 28, 2018

(86) PCT No.: PCT/HU2018/050053
§ 371 (c)(1),
(2) Date: Jun. 26, 2020

(87) PCT Pub. No.: WO2019/130030
PCT Pub. Date: Jul. 4, 2019

(65) Prior Publication Data
US 2021/0059812 A1    Mar. 4, 2021

(30) Foreign Application Priority Data
Dec. 28, 2017  (HU) .................................. P1700547

(51) Int. Cl.
*A61F 2/16*        (2006.01)

(52) U.S. Cl.
CPC ...... *A61F 2/1654* (2013.01); *A61F 2240/001* (2013.01)

(58) Field of Classification Search
CPC .. G02C 7/024; A61F 2/1654; A61F 2240/001; A61F 2/1618
See application file for complete search history.

(56) References Cited

U.S. PATENT DOCUMENTS

| 4,210,391 | A | * | 7/1980 | Cohen | ................. | G02B 5/1876 |
|           |   |   |        |       |                  | 359/743 |
| 9,320,594 | B2 | * | 4/2016 | Schwiegerling | ...... | A61F 2/1451 |

(Continued)

FOREIGN PATENT DOCUMENTS

WO        9744689 A1    11/1997

*Primary Examiner* — Megan Y Wolf
*Assistant Examiner* — Yasniary De La Caridad Morales
(74) *Attorney, Agent, or Firm* — Olson & Cepuritis, Ltd.

(57) ABSTRACT

The invention relates to an artificial ophthalmic lens (20) containing an anterior optical surface (21) and a posterior optical surface (22), at least one of which contains a multifocal optical diffractive profile (25). A cross apodized profile part (25') is formed on the diffractive profile (25) wherein phase shifting elements (27) are provided alternately forming the elements of a decreasingly apodized series (40) and an increasingly apodized series (41) in such a way that the decreasing and increasing elements of the two series (40, 41) form envelope curves that meet at a common intersection point (45).

The invention further relates to a method for the production of such an artificial ophthalmic lens (20).

10 Claims, 6 Drawing Sheets

(56) References Cited

U.S. PATENT DOCUMENTS

| | | |
|---|---|---|
| 10,842,617 B2 * | 11/2020 | Hong ................... G02B 3/08 |
| 2007/0258143 A1 | 11/2007 | Portney |
| 2012/0224138 A1 | 9/2012 | Cohen |
| 2017/0252151 A1 * | 9/2017 | MacKool ............. G02B 5/1895 |

* cited by examiner

DIFFRACTIVE ARTIFICIAL OPHTHALMIC LENS WITH OPTIMISED APODIZATION AND METHOD FOR THE PRODUCTION OF SUCH ARTIFICIAL OPHTHALMIC LENS

CROSS-REFERENCE TO RELATED APPLICATIONS

This application is a U.S. National Stage of PCT/HU2018/050053, filed Dec. 28, 2018, which claims priority to Hungarian National Application Number P1700547, filed Dec. 28, 2017, each of which is incorporated herein by reference.

OBJECT OF THE INVENTION

The object of the invention relates to an artificial ophthalmic lens that creates a suitably sharp image on the retina of objects located at far distances (>4 m), working distance 80 cm) and at reading distance (≈40 cm). The artificial ophthalmic lens described in the present invention may be implanted in the capsular bag, the ciliary sulcus or in the anterior chamber; it may be a contact lens, or an artificial lens that can be implanted in the cornea using an inlay or onlay technique. The object of the invention also relates to a method for the production of the aforementioned multifocal artificial ophthalmic lens.

STATE OF THE ART

The human crystalline lens transmits the large proportion of the visible range of the electromagnetic spectrum, as a result of advanced age, trauma, or extreme doses of UV or x-ray radiation the human eye may gradually become cloudy, which condition is called cataract. In addition, congenital cataract also exists, which can be inherited or the result of an infection during pregnancy. At present, the only effective way of treating cataracts is the removal of the clouded lens and the substitution of the refractive power of the lens by an implanted artificial ophthalmic lens.

A further indication for the implanting of an artificial ophthalmic lens may be a refractive defect of such an extent that the correction is not or only partially possible with spectacles, contact lenses, or corneal laser surgery. This procedure is called a refractive lens exchange.

Up until the second half of the nineteen-eighties, implanted artificial ophthalmic lenses were only monofocal lenses that formed a sharp image on the retina of objects at a given distance (usually further than 4 metres away).

The refractive multifocal artificial ophthalmic lenses available from the nineteen-nineties contain concentric or asymmetric zones with differing refractive power. Their disadvantage is that their optical performance strongly depends on pupil size; in addition, the intensity distribution of the incoming light in the vicinity of the retina does not vary smoothly as a function of the pupil diameter.

The diffractive, bifocal artificial ophthalmic lenses appearing in the 2000-s were also capable of creating sharp images on the retina of objects at reading distance (approximately 35 to 40 cm), however these artificial ophthalmic lenses were also unable to replace the accommodating ability of the natural human eye lens.

As a result of the increasingly widespread activities today performed with screens, the significance of the quality of images at intermediate distances (approximately 60 to 80 cm) has increased. The diffractive trifocal artificial ophthalmic lenses widely used by the 2010-s are able to satisfy this demand.

With the progression of age, the accommodating ability of the eye deteriorates as a result of the drop in flexibility of the natural human crystalline lens and of the weakening of the ciliary muscles. This eye-ageing condition is called presbyopia. Due to the availability of trifocal and extended depth of focus (EDOF) artificial ophthalmic lenses, artificial ophthalmic lens implants for other than cataract surgery do not only represent a purely refractive lens exchange, their purpose may also be to make up for accommodation ability. As implants made for reasons other than cataract surgery typically involve the younger (45- to 50-year-old) active age group, there is a significant demand for sharp sight at working distances (60 to 80 cm) in addition to far and near distances.

U.S. Pat. No. 5,344,447A (Swanson) describes a diffractive binary (Dammann) surface profile that creates three foci by amplifying the $-1^{st}$, the $0^{th}$ and the $+1^{st}$ diffraction orders. The disadvantage of this solution is that the intensity ratios falling on the $-1^{st}$ and $+1^{st}$ orders are the same and cannot be changed independently of each other.

The common characteristic of the diffractive surface profiles presented in the following two patent applications is that the $0^{th}$ order realises the focal point responsible for far sight, the $+1^{st}$ order realises the intermediate sight focal point, and the $+2^{nd}$ order realises the near sight focal point.

Patent specification number EP2503962 (A1) (Houbrechts et al.) presents a design method the basis of which is the combination (superposition) of two bifocal diffractive surface profiles, where the first diffraction order of the so-called first diffractive surface profile and the second diffraction order of the so-called second diffractive surface profile coincide. Consequentially, the three focus points are created by the $0^{th}$, $+1^{st}$ and the $+2^{nd}$ diffraction orders within the superimposed diffractive surface profile.

Patent application number US2011292335 (Schwiegerling) discloses a diffractive surface profile in which the height of the steps of the even numbered and odd numbered phase shifting elements, counted from the optical axis, changes. Another possible embodiment of the solution is a diffractive surface profile in which the height of the steps of the even numbered and odd numbered phase shifting elements, counted from the optical axis, changes and the step heights of the even numbered and odd numbered phase shifting elements are individually changed by individual apodization functions. Such diffractive surface profiles also achieve trifocal optical performance with the amplification of the $0^{th}$, the $+1^{st}$ and $+2^{nd}$ diffraction orders.

The common characteristic of the diffractive surface profiles presented up to this point is that the phase shifting elements have the same area and the ratio of the light output distributed between the individual focal points may be determined with the step heights of the phase shifting elements.

Patent application number US20120224138 (Cohen) discloses a design method suitable for the realisation of trifocal optical elements in which the phase shifting elements of the diffractive surface profile do not have the same area, therefore the intensity distribution realised between the individual focal points is realised jointly by the area of the phase shifting elements and by their step heights.

The commercially available AT LISA tri 839MP (Carl Zeiss Meditec AG, Germany, Jena) is a trifocal-bifocal intraocular lens that contains a trifocal diffractive profile in the inner 4.34 mm range, and a bifocal diffractive profile in the diameter range greater than 4.34 mm. The disadvantage of this solution is that the optical performance of the lens is not suitably pupil-dependent, and a sharp boundary may be found between the trifocal and the bifocal zones.

Patent application number US20070182921 (Zhang et al.) describes the simultaneous use of a saw tooth type, bifocal diffractive surface profile (in the outer zone of the intraocular lens) and of a binary (Dammann) type trifocal diffractive surface profile (in the inner zone of the intraocular lens). The disadvantage of this solution is also that in the case of small pupil sizes the intensity ratios in the $-1^{st}$ and $+1^{st}$ diffraction orders are the same and cannot be changed independently of each other.

The diffractive surface profile presented in patent application number EP3130314 (Pagnoulle et al.) discloses a trifocal diffractive surface profile that limits chromatic aberration in which the focal points responsible for far, intermediate and near vision are formed by the $+1^{st}$, $+2^{nd}$ and $+3^{rd}$ diffraction orders, in that order.

Patent application number EP3150169 (A1) (Lux et al.) discloses a diffractive surface profile that may be produced as the combination (superposition) of two different types of diffractive profile. The example presented may be produced as a combination of a conventional kinoform, bifocal diffractive surface profile and a binary (Dammann) type diffractive surface profile.

A common characteristic of the solutions mentioned above and of the trifocal-bifocal lenses commercially available is that their trifocal and bifocal ranges are sharply separated. In these solutions the multifocality of the trifocal range is realised with the enhancement of the $-1^{st}$, $0^{th}$ and $+1^{st}$ diffraction orders, or with the enhancement of the $0^{th}$, $+1^{st}$ and $+2^{nd}$ diffraction orders. In these cases the multifocality of the bifocal range is realised with a conventional saw-tooth-type diffractive profile.

A known technique in the case of designing diffractive profiles is the so-called apodization. This means a reduction of the height of the diffractive steps, and with this a reduction of the effect of the diffractive order towards the periphery, i.e. for the case of increasing apertures. Some of the aforementioned solutions apply apodization.

BRIEF SUMMARY OF THE INVENTION

The objective of the invention is to overcome the deficiencies of the known solutions at least partially and to create a multifocal artificial ophthalmic lens with the help of which the intensity distribution changes as a function of pupil diameter in such a way that the multifocality, i.e. the number of foci, may also be varied, in consideration of the most probable sharp vision distance demand occurring in the case of the given (illumination-dependent) pupil diameter.

The inventors have recognised that a trifocal-bifocal optical element can be realised in a different way than the known combination of two diffractive profiles operating differently from the point of view of the enhanced diffraction orders. The inventors have recognised that by applying suitable apodization it is possible to ensure a continuous transition in the operation of a saw-tooth type diffractive profile from trifocal optical performance to bifocal optical performance which takes place dependent on the pupil size.

The present invention describes a diffractive profile that shifts continuously from trifocal optical performance to characteristically bifocal optical performance with the increase of the diameter of the aperture, in other words, of the pupil. Such a trifocal-bifocal performance lens is able to simultaneously ensure the advantages of trifocal and bifocal lenses. Thus, extremely great trifocal optical performance can be achieved in the case of small apertures ensuring better intermediate distance vision than the prior art solutions while it is possible to simultaneously retain more moderate trifocal performance for greater apertures which is widespread and appreciated in clinical practice.

The object of the present invention relates to an artificial ophthalmic lens that contains an anterior optical surface and a posterior optical surface. The anterior optical surface and the posterior optical surface have a common optical axis. At least one of the anterior optical surface and the posterior optical surface is a multifocal optics that has multifocal optical performance which is partly or entirely ensured by a diffractive profile. It shifting elements are provided on the diffractive profile with at least one decreasing apodization, and with at least one increasing (reversed) apodization, which meet, i.e. they have a common intersection point.

A preferred embodiment of the invention relates to a multifocal optics in which the diffractive profile is surrounded by a purely refractive zone with monofocal optical performance. Another possible embodiment relates to a multifocal optics in which the diffractive profile covers the entire optical surface.

The object of the invention also relates to a method with which the above artificial ophthalmic lens can be produced.

BRIEF DESCRIPTION OF DRAWINGS

FIG. 4b shows the simulated modulation transfer function (MTF) of an artificial ophthalmic lens in accordance with FIG. 3a.

DETAILED DESCRIPTION OF THE EMBODIMENTS ACCORDING TO THE INVENTION

The artificial ophthalmic lens described in the present invention may be an artificial lens implanted in the capsular bag, the ciliary sulcus or in the anterior chamber, and may be a contact lens, or an artificial lens that can be implanted in the cornea using an inlay or onlay technique. The Figures presented above relate to some types of the implantable artificial lens, but other lens types may also be formed using the principle according to the invention.

Figure 1:
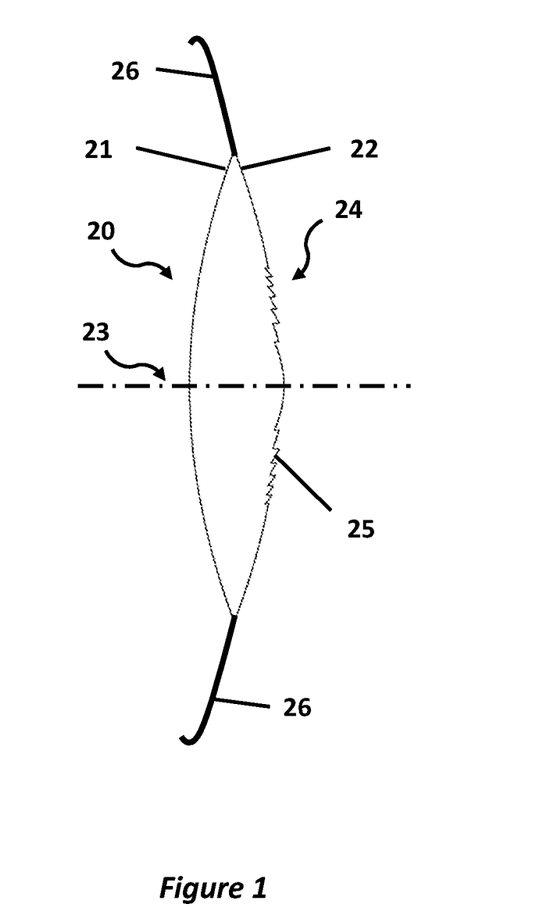
FIG. 1 depicts a schematic side view of an exemplary embodiment of the present invention.

FIG. 1 depicts a schematic side view of an exemplary embodiment of an artificial ophthalmic lens 20 according to the present invention, in which it can be seen that the artificial ophthalmic lens 20 contains an anterior optical surface 21 and a posterior optical surface 22. The anterior optical surface 21 and the posterior optical surface 22 have a common optical axis 23. In the case of the present embodiment the posterior optical surface 22 is formed as a multifocal optics 24, which partly has a multifocal optical diffractive profile 25. The present embodiment is also provided with haptics 26, since an implantable artificial lens is shown in FIG. 1.

Figure 2A:
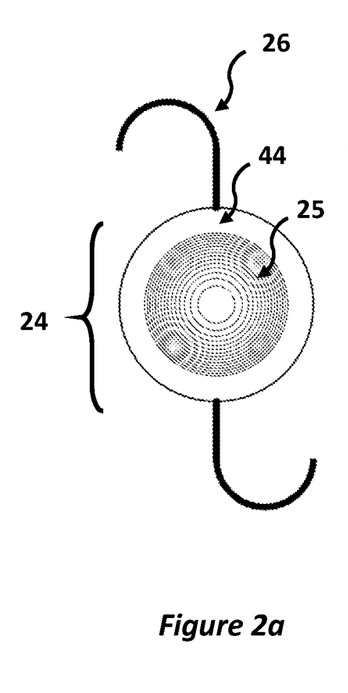
FIG. 2a depicts a front view of an exemplary embodiment of the artificial ophthalmic lens according to the invention.

FIG. 2a depicts a front view of a possible embodiment of the artificial ophthalmic lens according to the invention, where the inner zone falling closer to the optical axis 23 of the multifocal optics 24 provided with haptics 26 has a multifocal optical diffractive profile 25, and a monofocal peripheral refractive zone 44 surrounding it.

Figure 2B:
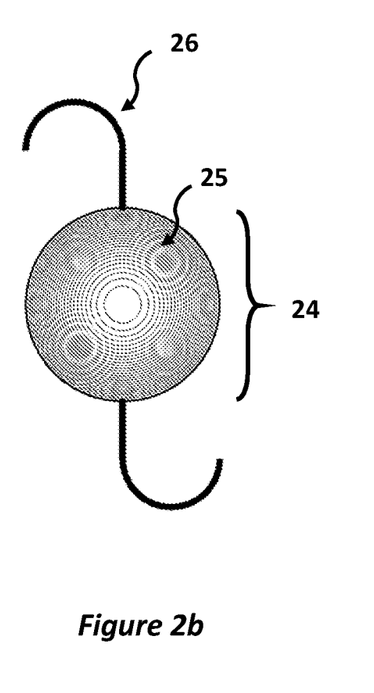
FIG. 2b depicts a front view of another exemplary embodiment of the artificial ophthalmic lens according to the invention.

FIG. 2b depicts a front view of another possible embodiment of the artificial ophthalmic lens according to the invention, where the entire multifocal optics 24, also provided with haptics 26, is provided with a multifocal optical diffractive profile 25.

A significant feature of the implementation of the multifocal (trifocal-bifocal) optical performance is the diffractive profile 25, which is located on the anterior optical surface 21 or the posterior optical surface 22 of the artificial ophthalmic lens. The phase shifting elements (phase shifting zones) closer to the optical axis 23 of the diffractive profile 25 at least partially form a profile that enhances three diffraction orders. The phase shifting elements further away from the optical axis 23 at least partially form a profile that enhances two diffraction orders when using an annular aperture centered on the optical axis 23.

An important feature of such a diffractive profile with trifocal-bifocal optical performance is the so-called cross apodized profile part ("cross apodization"). A possible implementation of cross apodization is that when starting from the optical axis 23 the height of every odd-numbered phase shifting element (in other words, the distance between the base point and the peak of the given phase shifting element) decreases monotonously as a function of distance from the optical axis 23, where a central zone is the first phase shifting element, and starting from the optical axis 23 the height of every even-numbered phase shifting element increases monotonously as a function of distance from the optical axis 23. Another implementation of cross apodization is that when starting from the optical axis 23 the height of every odd-numbered phase shifting element increases monotonously as a function of distance from the optical axis 23, where a central zone is the first phase shifting element, and starting from the optical axis 23 the height of every even-numbered phase shifting element decreases monotonously as a function of distance from the optical axis 23.

Figure 3A:
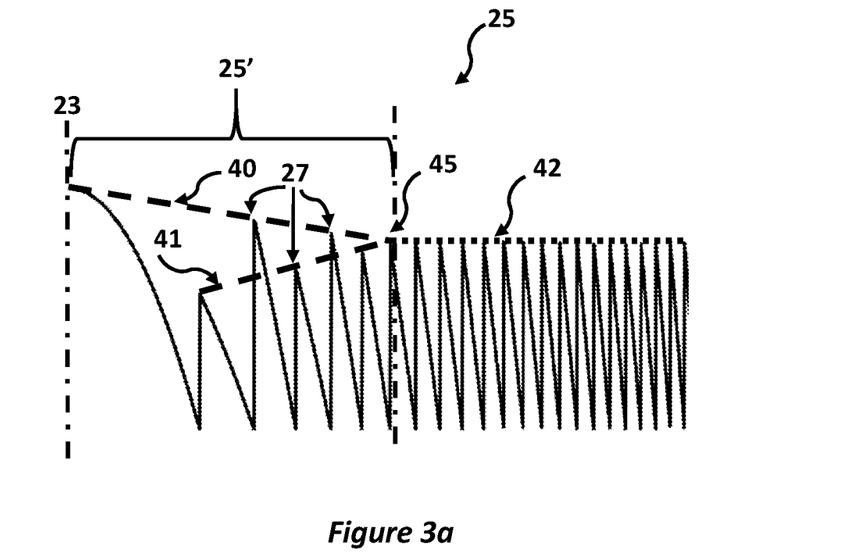
FIG. 3a depicts an embodiment of the artificial ophthalmic lens according to the invention where the decreasing and increasing (reversed) apodizations meet at a common intersection point within the diffractive profile, while the part of the diffractive profile outside of the intersection point is non-apodized.

FIG. 3a depicts a possible implementation of the multifocal optics with trifocal-bifocal optical performance in which the phase shifting elements 27 of the cross apodized profile part 25' of the diffractive profile 25 can be divided, in a direction perpendicular to the optical axis 23, into a decreasingly apodized series 40 and an increasingly (reversed) apodized series 41. In other words cross apodization is provided, at least partly, on the diffractive profile 25. The decreasing and increasing elements of the series 40 and 41 meet at a common intersection point 45, in other words, envelope curves that intersect at the common intersection point 45 may be fitted onto the phase shifting elements of the decreasing apodization series 40 and onto the phase shifting elements of the increasingly apodized series 41, as it can be seen in FIGS. 3a to 3d. In the case of the present examples the envelope curves are straight lines, but, naturally, other shaped envelope curves are conceivable, such as envelope curves that decrease or increase according to a polynomial function.

In FIG. 3a the intersection point 45 is at the boundary of the cross apodized profile part 25', other embodiments are also conceivable in the case of which the intersection point 45 is within the boundary of the cross apodized profile part 25' (see FIG. 3c), or in the case of which the intersection point 45 is outside of the boundary of the cross apodized profile part 25'. In 44 other words, the phase shifting elements 27 of the decreasingly apodized series 40, and the phase shifting elements 27 of the increasingly apodized series 41 do not actually meet in size. In the case of a particularly preferred embodiment, the intersection point 45 is on the external boundary of the cross apodized profile part 25', whereby the profile of the artificial ophthalmic lens 20 outside of this boundary may be continued at the height of the intersection point, as it can be seen in the case of the present embodiment. In the present case a non-apodized diffractive profile part 42 is provided outwards from the intersection point 45 (in other words, moving outwards in the radial direction perpendicular to the optical axis 23). The heights of the phase shifting zones of the non-apodized diffractive profile part 42 are the same, and its optical performance is bifocal. In the case of this embodiment the non-apodized diffractive profile part 42 forms a circular ring symmetrical around the optical axis 23. In other words, in the case of this embodiment the diffractive profile 25 contains the central cross apodized profile part 25', and the non-apodized diffractive profile part 42 surrounding it peripherally.

Figure 3B:
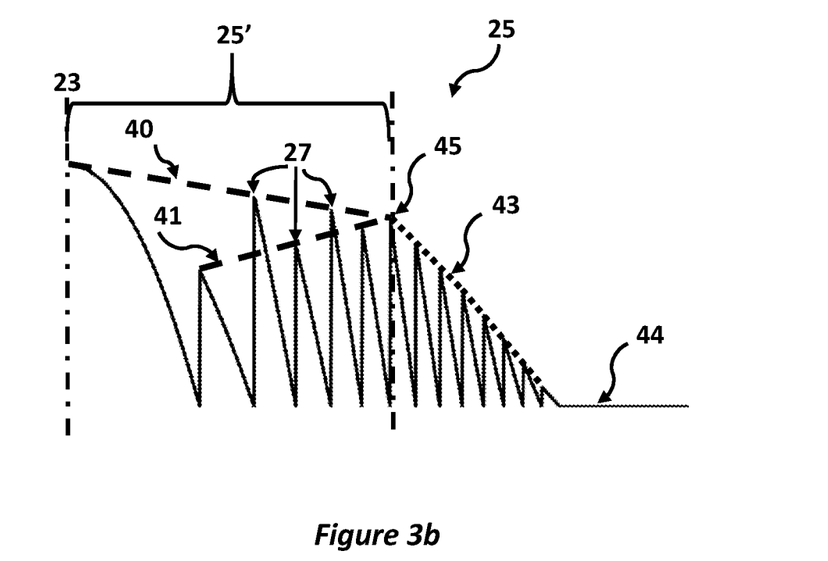
FIG. 3b depicts an embodiment of the artificial ophthalmic lens according to the invention where the decreasing and increasing (reversed) apodizations meet at a common intersection point within the diffractive profile, while the part of the diffractive profile peripheral with respect to the intersection point is decreasingly apodized, and the multifocal optics contains further refractive zones peripheral to (outside of) the cross apodized diffractive profile.

In FIG. 3b a different exemplary embodiment of the multifocal optics with trifocal-bifocal optical performance can be seen, in the case of which the central cross apodized profile part 25' of the diffractive profile 25 is formed by a decreasingly apodized series 40 and by an increasingly (reversed) apodized series 41 of phase shifting elements 27 in a direction perpendicular to the optical axis 23, the envelope curves of which meet at a common intersection point 45; in other words, the central part of the diffractive profile 25 is "cross apodized". The diffractive profile 25 is formed as a diffractive profile part 43 that is decreasingly apodized outwards from the intersection point 45 perpendicular to the optical axis. The apodized diffractive profile 43, similarly to the non-apodized diffractive profile 42, preferably surrounds the inner part of the diffractive profile 25 in a ring shape. In the case of this embodiment the multifocal optics 24 is provided with a refractive zone peripherally surrounding the diffractive profile 25.

Figure 3C:
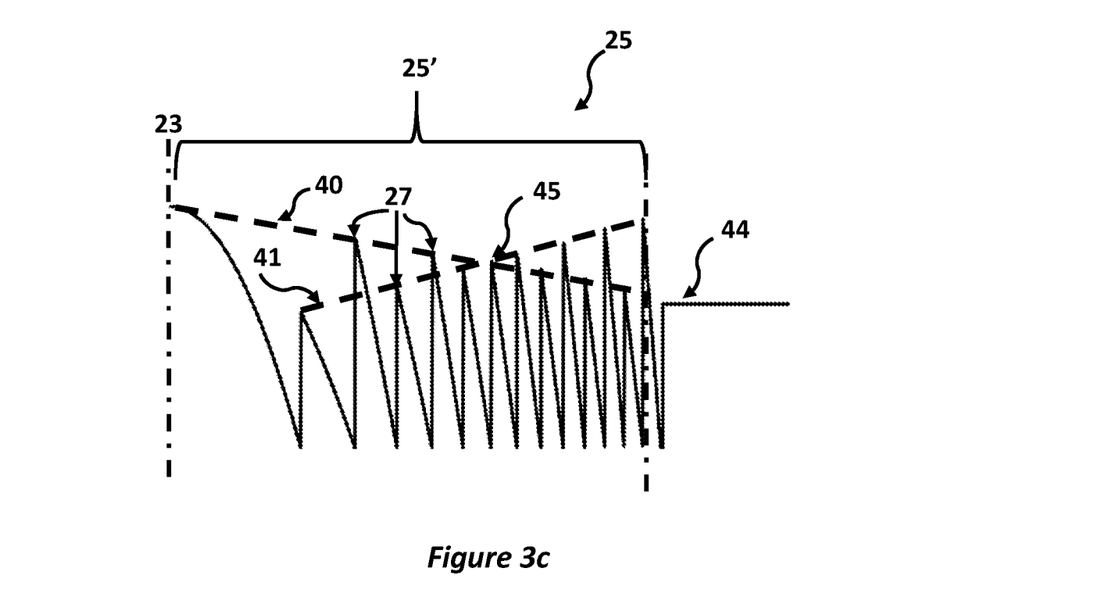
FIG. 3c depicts an embodiment of the artificial ophthalmic lens according to the invention where the decreasing and increasing (reversed) apodizations meet at a common intersection point within the diffractive profile and continue beyond the intersection point, and the multifocal optics contains further refractive zones peripheral to the cross apodized diffractive profile.

FIG. 3*c* presents a different possible embodiment of the multifocal optics with trifocal-bifocal optical performance according to the invention, in which the phase shifting elements 27 of the diffractive profile 25 form a decreasingly apodized series 40 and an increasingly (reversed) apodized series 41 alternatingly in a direction perpendicular to the optical axis 23 in such a way that the common intersection point 45 of the envelope curves fitted onto the decreasing and increasing elements of the two series 40, 41 fall within the boundary of the cross apodized profile part 25' of the diffractive profile 25, as opposed to the previously shown embodiments, in the case of which the intersection point 45 falls on the boundary of the cross apodized profile part 25'. In the case of the present embodiment the cross apodized profile part 25' of the diffractive profile 25 continues outwards from the intersection point 45 in such a way that the elements of the decreasingly apodized series 40 and the increasingly (reversed) apodized series 41 continue to be provided beyond the common intersection point 45. In the case of this embodiment the multifocal optics 24 is also provided with a refractive zone 44 peripherally surrounding the diffractive profile 25.

Figure 3D:
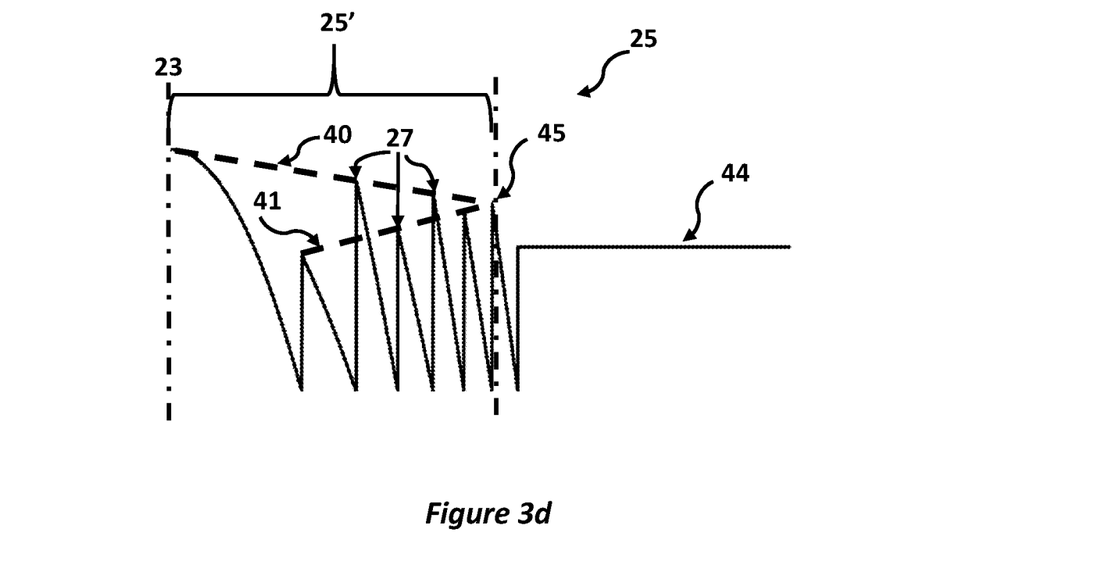
FIG. 3d depicts an embodiment of the artificial ophthalmic lens according to the invention where the decreasing and increasing (reversed) apodizations meet at a common intersection point within the diffractive profile and continue beyond the intersection point, and the multifocal optics contains further refractive zones peripheral to the intersection point.

FIG. 3*d* presents a preferred embodiment of the multifocal optics 24 with trifocal-bifocal optical performance in which the entire diffractive profile 25 can be divided, in a direction perpendicular to the optical axis 23, into a decreasingly apodized series 40 and an increasingly (reversed) apodized series 41 of phase shifting elements 27. The boundary of the phase shifting zone of the diffractive profile most distant from the optical axis 23 essentially coincides with the intersection point 45, in other words, with the intersection point of the envelope curves that can be fitted onto the phase shifting elements 27 of the series 40, 41. In other words, the diffractive profile 25 is formed substantially until the intersection point 45. The phase shift of the first (odd numbered) phase shifting element 27 of the embodiment presented in FIG. 3*d* falls in the range of 0.55 . . . 0.59·λ, while the phase shift of the second (even numbered) zone falls in the range of 0.30 . . . 0.34·λ. The phase shift of the phase shifting elements 27 of the decreasingly apodized series 40 (odd numbered zones) is a monotonously decreasing function of distance measured from the optical axis 23. The phase shift of the phase shifting elements 27 of the series 41 (even numbered zones) is a monotonously increasing function of distance measured from the optical axis 23. The phase shift of the phase shifting elements 27 at the intersection point 45 of the diffractive profile 25 is in the range 0.42 . . . 0.46·λ.

The total number of the phase shifting elements 27 in the cross apodized profile part 25' of the diffractive profile 25 is preferably between five and twenty, even more preferably between five and seven, still even more preferably seven.

The cross apodized profile part 25' of the diffractive profile 25 may be combined with any known lens structure, in other words, the artificial ophthalmic lens may be toric, aspherical or free-form.

Figure 4A:
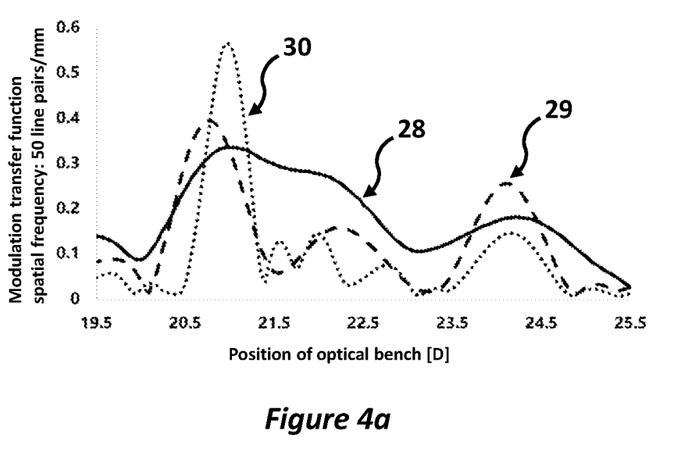
FIG. 4a shows the modulation transfer function (MTF) of an artificial ophthalmic lens in accordance with FIG. 3d and measured using an instrument operating as an optical bench.

The quantitative assessment of the image formation of the embodiment illustrated in FIG. 3*d* can be seen in FIG. 4*a*, which shows the modulation transfer function (MTF) of the artificial ophthalmic lens 20 according to the present invention measured on an optical bench at a spatial frequency of 50 line pairs/mm. The curve 28 shown with solid line relates to a test aperture diameter of 2.0 mm, the curve 29 shown with dashed line relates to an aperture of 3.0 mm, and the curve 30 shown with dotted line relates to an aperture of 4.5 mm, which apertures correspond to the various typical pupil diameters. In the present case the intersection point 45 is located at 1.5 mm from the optical axis 23; in other words, the radius of the aperture belonging to the broken line curve 29 extends until the intersection point 45, The MTF curves illustrate how the image formation quality changes as a function of object distance. The MTF curves obtained at the various apertures are determined by the depth of focus dependent on aperture diameter and by the intensity distribution together. As demonstrated by FIG. 4 it may be determined that in the case of a small aperture (narrow pupil), when the phase shifting elements 27 of the diffractive profile closest to the optical axis 23 take part in the image formation, the MTF curve (solid line curve 28) displays extremely great trifocality. It can be clearly seen on the solid line curve 28 that the proximity of the peaks corresponding to the two most distant foci results in an extended depth of focus (EDoF), which ensures better intermediate distance vision for the user. The great degree of trifocality occurring at small apertures, and the aforementioned EDoF optics are the result of the large height differences between the phase shifting elements 27 of decreasing and increasing height close to the optical axis 23. This height difference drops moving away from the optical axis as a result of the cross apodization according to the invention up until the intersection point 45, which also results in the reduction in trifocality (see dashed line curve 29), In practice, the dashed line curve 29 corresponds to an optical performance similar to the trifocal lenses used widely in clinical practice. Therefore, the artificial ophthalmic lens 20 according to the invention retains the proven characteristic shown by the broken line 29 while at the same time it is capable of ensuring imaging properties that produce better intermediate vision in the case of smaller apertures.

By increasing the aperture beyond the intersection point 45 the refractive zone 44 also becomes involved in the imaging, which reduces the trifocal character even more, Therefore, the dotted line curve 30 belonging to the largest aperture is mainly monofocal.

Figure 4B:
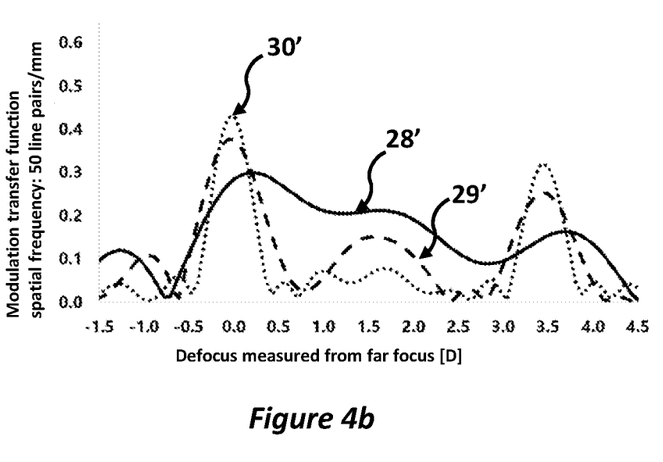

FIG. 4*b* illustrates the imaging of the artificial ophthalmic lens 20 according to FIG. 3*a*. The solid line curve 28' relates to a 2.0 mm diameter test aperture, the broken line curve 29' to a 3.0 mm aperture, and the dotted line curve 30' to a 4.5 mm aperture. With the appropriate selection of the zone around the periphery of the cross apodized profile part 25' of the diffractive profile 25 various types of optical performance can be created at the largest apertures in accordance with the various demands. For example, the dotted line curve 30 shown in FIG. 4*a* displays a substantially monofocal optical performance, but the dotted line curve 30' in FIG. 4*b* is purely bifocal as a consequence of the non-apodized diffractive profile part 42. With the increase of the size of the pupil the optical performance of the embodiment presented in FIG. 3*b* changes from trifocal to bifocal and monofocal. With the increase of the size of the pupil the embodiment presented in FIG. 3*c* changes from trifocal to bifocal, then again into trifocal (MTF curves not illustrated).

Figure 5:
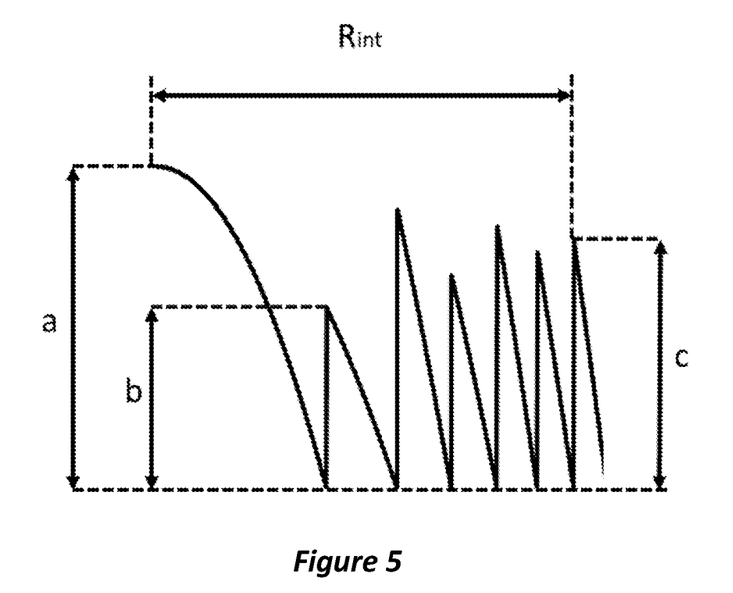
FIG. 5 depicts a schematic diagram showing the possible dimensioning of the phase shifting elements of the cross apodization according to the invention.

FIG. 5 depicts a schematic diagram illustrating the possible dimensioning of the phase shifting elements of the cross apodization according to the invention, where the letters "a, b and c" mark the height of the central zone (first phase shifting element), of the phase shifting element next to the central zone, and of the phase shifting element at the intersection point 45, respectively, and Rint refers to the distance of the intersection point 45 from the optical axis 23.

It should be noted that in the case of those embodiments where the intersection point 45 is further outside from the boundary of the cross apodized profile part 25', the height "c" can be determined indirectly, such as by using interpolation. For the diffractive profile 25 according to the invention the ratio of the b/a heights is preferably between 0.30 and 0.95, more preferably between 0.4 and 0.70, and the ratio of the c/a heights is preferably between the b/a height and 1. The distance Rint of the intersection point 45 from the optical axis 23 is preferably between 0.6 mm and 3.0 mm, more preferably between 1.25 mm and 2.5 mm.

The invention also relates to a method for the production of an artificial ophthalmic lens 20 that contains an anterior optical surface 21 and a posterior optical surface 22, where the anterior optical surface 21 and the posterior optical surface 22 have a common optical axis 23, and at least either the anterior optical surface 21 or the posterior optical surface 22 is a multifocal optics 24 that has at least a partially multifocal optical diffractive profile 25.

In the course of the method according to the invention cross apodization, determined by the phase shifting elements 27 of a decreasingly apodized series 40 and of an increasingly (reversed) apodized series 41, is provided on the diffractive profile 25 at least partially in such a way that the decreasing and increasing phase shifting elements 27 of the series 40, 41 meet at a common intersection point 45.

In the case of a preferred embodiment of the method according to the invention, the phase shifting elements 27 are produced using a material removal process, or hot forming, preferably or injection moulding.

The advantage of the present invention is that depending on the diameter of the pupil various intensity distributions can be created, and the number of focal points can also be varied.

The invention claimed is:

1. A multifocal artificial ophthalmic lens that contains an anterior optical surface and a posterior optical surface, where the anterior optical surface and the posterior optical surface have a common optical axis and at least one of the anterior optical surface and the posterior optical surface is a multifocal optics comprising a multifocal optical diffractive profile that shifts continuously from trifocal performance to bifocal performance with an increase of a diameter of an aperture, wherein a cross apodized profile part is formed on the diffractive profile, and five to twenty phase shifting elements are provided next to each other on the diffractive profile that alternately form the elements of a decreasingly apodized series and an increasingly (reversed) apodized series in such a way that the decreasing and increasing elements of the two series define envelope curves that meet at a common intersection point.

2. The multifocal artificial ophthalmic lens according to claim 1, wherein starting from the optical axis the height of every odd-numbered phase shifting element decreases monotonously as a function of distance from the optical, and the height of every even-numbered phase shifting element increases monotonously as a function of distance from the optical axis.

3. The multifocal artificial ophthalmic lens according to claim 1, wherein starting from the optical axis the height of every odd-numbered phase shifting element increases monotonously as a function of distance from the optical axis, and the height of every even-numbered phase shifting element decreases monotonously as a function of distance from the optical axis.

4. The multifocal artificial ophthalmic lens according to claim 1, wherein the diffractive profile contains a non-apodized diffractive profile part that peripherally surrounds the cross apodized profile part.

5. The multifocal artificial ophthalmic lens according to claim 1, wherein the diffractive profile contains an apodized diffractive profile part that peripherally surrounds the cross apodized profile part.

6. The multifocal artificial ophthalmic lens according to claim 1, wherein the common intersection point of the envelope curves is at or within a boundary of the cross apodized profile part of the diffractive profile.

7. The multifocal artificial ophthalmic lens according to claim 1, wherein the entire diffractive profile is cross apodized.

8. The multifocal artificial ophthalmic lens according to claim 1, wherein the multifocal optics has a purely refractive optical refractive zone peripherally surrounding the diffractive profile.

9. The multifocal artificial ophthalmic lens according to claim 1, further comprising haptics.

10. The multifocal artificial ophthalmic lens according to claim 1, wherein the number of the phase shifting elements in the cross apodized profile part of the diffractive profile is between five and seven.

* * * * *